(12) United States Patent
Sugimoto

(10) Patent No.: US 7,907,169 B2
(45) Date of Patent: Mar. 15, 2011

(54) ELECTRONIC ENDOSCOPE SYSTEM FOR FLUORESCENCE OBSERVATION

(75) Inventor: Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 1589 days.

(21) Appl. No.: 11/186,905

(22) Filed: Jul. 22, 2005

(65) Prior Publication Data

US 2006/0020169 A1  Jan. 26, 2006

(30) Foreign Application Priority Data

Jul. 23, 2004 (JP) .................................. 2004-215597

(51) Int. Cl.
*H04N 7/18* (2006.01)

(52) U.S. Cl. .......................................... 348/65; 348/68

(58) Field of Classification Search ............... 348/65–76
See application file for complete search history.

(56) References Cited

U.S. PATENT DOCUMENTS

| | | | |
|---|---|---|---|
| 6,099,466 A | 8/2000 | Sano et al. | |
| 6,319,198 B1 | 11/2001 | Takahashi | |
| 6,537,211 B1 * | 3/2003 | Wang et al. | 600/178 |
| 6,687,534 B2 | 2/2004 | Tsujita | |
| 2002/0016620 A1 | 2/2002 | Tsujita | |

FOREIGN PATENT DOCUMENTS

| | | |
|---|---|---|
| JP | 7-155292 | 6/1995 |
| JP | 9-066023 | 3/1997 |
| JP | 9-66023 | 3/1997 |
| JP | 9-253039 | 9/1997 |
| JP | 10-151104 | 6/1998 |
| JP | 2000-134610 | 5/2000 |
| JP | 2002-045329 | 2/2002 |
| JP | 2003-033324 | 2/2003 |
| JP | 2003-33324 | 2/2003 |
| JP | 2003-179785 | 6/2003 |

OTHER PUBLICATIONS

English Language abstract of JP 9-66023.

* cited by examiner

*Primary Examiner* — Andy S Rao
(74) *Attorney, Agent, or Firm* — Greenblum & Bernstein, P.L.C.

(57) ABSTRACT

An electronic endoscope system, which is adapted to observe a fluorescence image of autofluorescence emitted from a body cavity wall irradiated with excitation light as well as a normal image of the body cavity wall illuminated with white light on a display device, includes a brightness control system configured to adjust brightness of at least one of the normal image and the fluorescence image to reduce brightness difference between the normal image and the fluorescence image to be displayed.

15 Claims, 7 Drawing Sheets

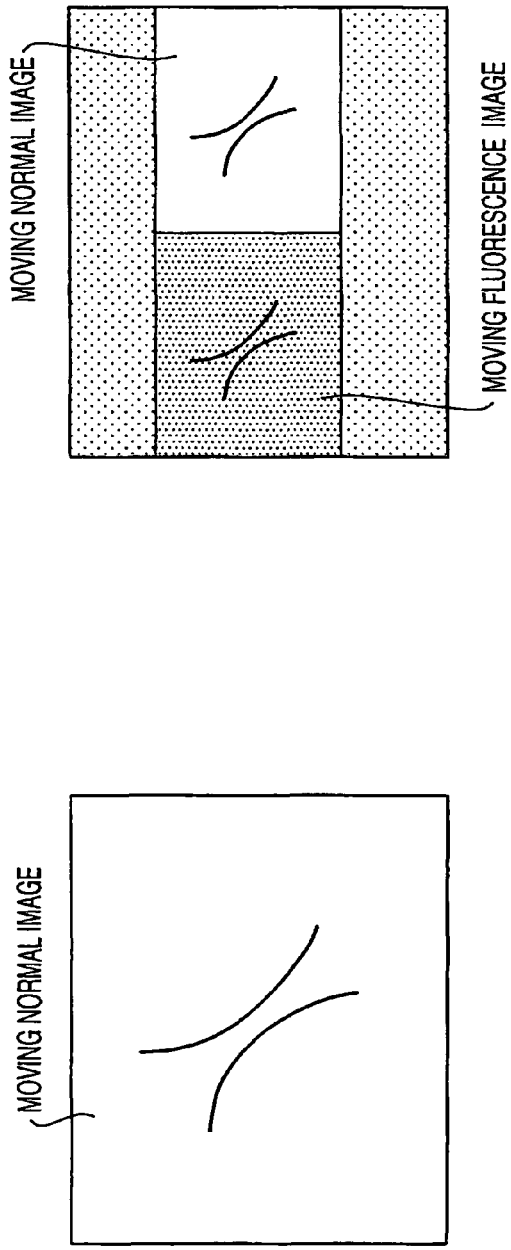
FIG. 7
FIG. 9
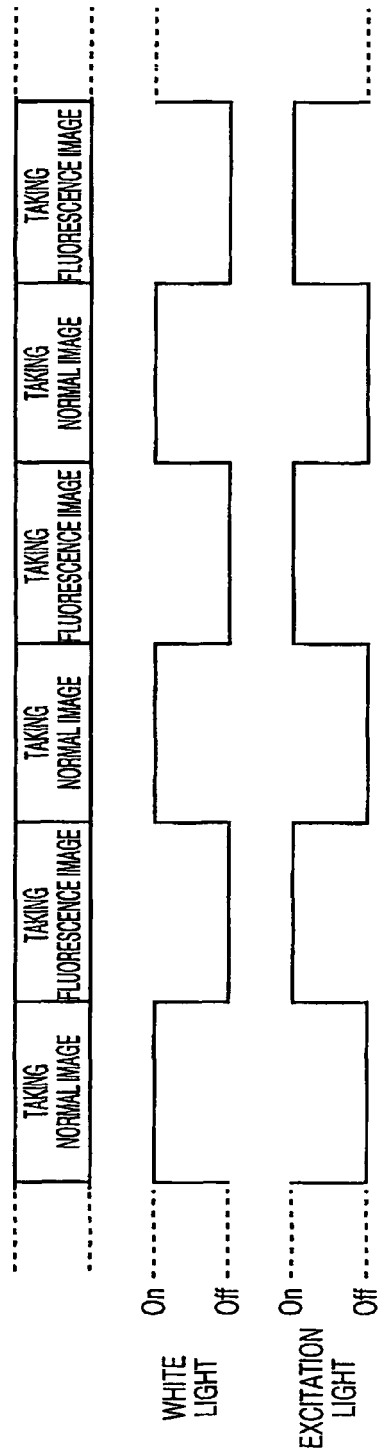
FIG. 8

ELECTRONIC ENDOSCOPE SYSTEM FOR FLUORESCENCE OBSERVATION

BACKGROUND OF THE INVENTION

The present invention relates to an electronic endoscope system that is adapted to observe a fluorescence image of autofluorescence emitted from a body cavity wall irradiated with excitation light, as well as a normal image of the body cavity wall illuminated with white light, on a display device such as a monitor.

An example of such an electronic endoscope system is disclosed in Japanese Patent Provisional Publications No. HEI 9-066023. The system disclosed in this publication includes a first solid-state imaging device that takes a fluorescence image, and a second solid-state imaging device that takes an RGB color image with illuminating light in accordance with a frame sequential method. In the system, signals outputted from the first and second solid-state imaging devices are processed by video circuits for fluorescence images and for normal images, respectively. The signals are then synthesized by an image synthetic circuit, and are displayed on a monitor device. According to the operation of a display image selector switch, one of the two kinds of images or both is displayed on the monitor device.

Another example is disclosed in Japanese Patent Provisional Publication No. P2003-33324A. FIG. 11 of the present application shows a block diagram of the system that is illustrated in FIG. 16 of Japanese Patent Provisional Publication No. P2003-33324A. The system disclosed in Japanese Patent Provisional Publication No. P2003-33324A includes (see FIG. 11) a first lamp 124 that emits illuminating light for normal observation and a second lamp 125 that emits excitation light, and either one of the two kinds of light is selectively introduced into a light guide 133 by changing the position of a movable mirror 128. Image signals captured by CCD 137 are stored in a first memory 141 and a second memory 142, and are then displayed on a Hi-Vision monitor 115 through a display location selector circuit 144. When a selector switch for displaying two images (hereinafter, referred to as a two-image-display switch) is turned ON, a normal image and a fluorescence image are displayed on the Hi-Vision monitor 115, simultaneously.

However, when the normal image and the fluorescence image are concurrently displayed as moving images, the brightness of the fluorescence image is dramatically low in comparison with the normal image. Therefore, when both kinds of images are displayed side by side on the monitor as the images are without modification, the great amount brightness difference causes a problem that an observer gets needlessly tired.

SUMMARY OF THE INVENTION

The present invention is advantageous in that an electronic endoscope system is provided that is capable of reducing observer's fatigue caused by great amount brightness difference when a normal image and a fluorescence image are displayed simultaneously.

According to an aspect of the invention, there is provided an electronic endoscope system used for observing living tissues inside a body cavity, provided with an image capturing system capable of capturing at least a normal image and a fluorescence image of the living tissues, an illuminating device having a white light source emitting white light and an excitation light source that emits excitation light having a predetermined wavelength, the living tissues emitting autofluorescence when irradiated with the excitation light, at least one display device configured to display the normal image and the fluorescence image, and a brightness control system configured to adjust brightness of at least one of the normal image and the fluorescence image to reduce brightness difference between the normal image and the fluorescence image to be displayed.

Optionally, the brightness control system may include brightness detectors configured to detect the brightness of the normal image and the fluorescence image and a brightness comparing system configured to compare the brightness between the normal image and the fluorescence image that are displayed simultaneously, the brightness control system controlling the brightness of at least one of the normal image and the fluorescence image that is detected by one of the brightness detectors to reduce the brightness difference between the normal image and the fluorescence image based on a comparison result analyzed by the brightness comparing system.

Further optionally, the normal image and the fluorescence image may be displayed simultaneously on the same display device.

Alternatively, the normal image and the fluorescence image may be displayed simultaneously on the separate display devices, respectively.

Furthermore, the brightness control system may include brightness detectors configured to detect the brightness of the normal image and the fluorescence image, a setting system configured to define a target value for the brightness of the normal image and the fluorescence image, and a brightness comparing system configured to compare the brightness of one of the normal image and the fluorescence image with the target value defined by the setting system, the brightness control system controlling the brightness of one of the normal image and the fluorescence image that is displayed on the display device, which is detected by one of the brightness detectors, to be substantially equal to the target value defined by the setting system based on a comparison result analyzed by the brightness comparing system when either one of the normal image and the fluorescence image is displayed on the display device.

Optionally, the brightness control system may include a white light control system configured to control the intensity of the white light to adjust the brightness of the normal image.

Further optionally, the white light control system may include an aperture control system configured to drive a light control aperture that changes the beam diameter of the white light to control the intensity of the white light.

Optionally, the aperture control system may include an aperture opening detector configured to detect the opening level of the light control aperture, the aperture control system using a detection result from the aperture opening detector to drive the light control aperture under closed-loop control.

Yet optionally, the brightness control system may include an excitation light control system configured to control the emission amount of the excitation light to adjust the brightness of the fluorescence image.

Still optionally, the brightness control system may include a multiplier configured to amplify or attenuate fluorescence image signals to adjust the brightness of the fluorescence image.

Furthermore, the electronic endoscope system may further include a ROM that stores an identification data for identifying the kind of electronic endoscope connected to the illuminating device.

Optionally, the illuminating device may include a rotary shutter provided in front of the white light source, the rotary shutter having a light transmitting area and a light blocking area, the white light intermittently illuminating the living tissues as the rotary shutter rotates.

Still further, the illuminating device may include an excitation light source driver that intermittently turns ON/OFF the excitation light source synchronously with blocking/transmitting of the white light.

Optionally, the image capturing system may include an objective lens that receives light from the living tissues and forms an image thereof, an imaging device that receives the formed image and outputs an image signal corresponding to the received image, and an excitation light cut filter configured to eliminate the wavelength components equivalent to the excitation light from light directed to the imaging device.

Optionally, the excitation light cut filter is provided between the imaging device and the objective lens.

Preferably, the excitation light source may emit near-ultraviolet light.

BRIEF DESCRIPTION OF THE ACCOMPANYING DRAWINGS

FIG. 7 shows an example of a screen displayed on a monitor in a normal image display mode;

FIG. 8 is a chart illustrating the respective irradiation timings of white light and excitation light and the respective timings when the two kinds of image data are outputted from an imaging device in a simultaneous display mode;

FIG. 9 shows an example of a screen displayed on the monitor in the simultaneous display mode;

DETAILED DESCRIPTION OF THE EMBODIMENTS

Hereinafter, an electronic endoscope system according to two embodiments of the present invention will be described with reference to the accompanying drawings. The electronic endoscope system of the embodiment is directed to a system that is adapted to observe a fluorescence image of autofluorescence emitted from a body cavity wall irradiated with excitation light on a display device such as a monitor, as well as a normal image of the body cavity wall illuminated with white light.

Figure 1:
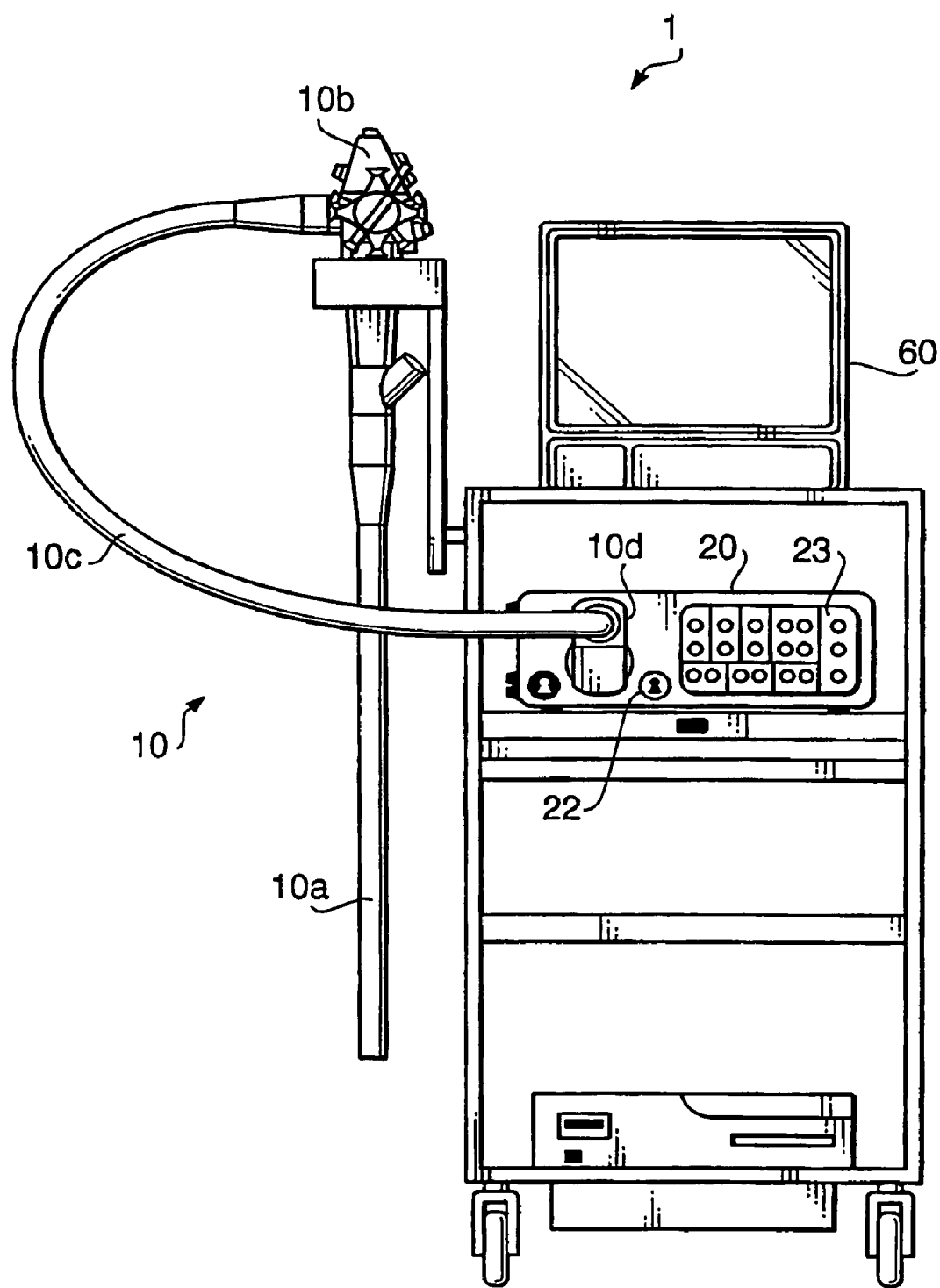
FIG. 1 is a front view of an electronic endoscope system according to a first embodiment of the invention.
Figure 2:
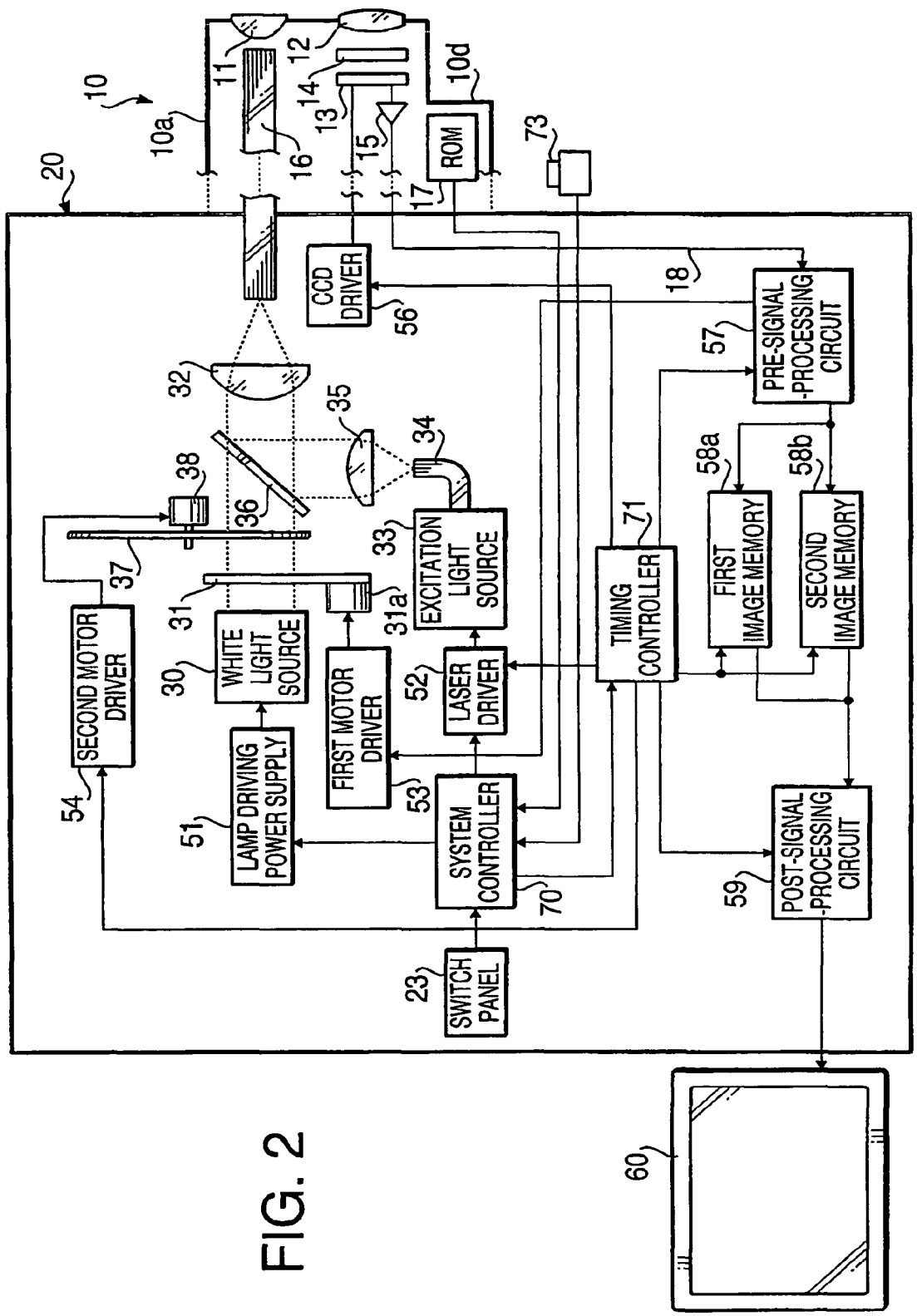
FIG. 2 is a block diagram illustrating internal constitution of the electronic endoscope system shown in FIG. 1.

FIG. 1 schematically shows an external view of an electronic endoscope system 1 according to a first embodiment of the invention, and FIG. 2 shows a block diagram illustrating an internal constitution of the electronic endoscope system 1. As shown in FIG. 1, the electronic endoscope system is provided with a fluorescence observation endoscope 10, a light source apparatus 20, and a monitor 60.

The fluorescence observation endoscope 10, which is adapted to fluorescence observation by modifying a usual electronic endoscope, is provided with an insertion part 10a that is formed long and slender so as to be inserted into the body cavity and has a flexible bendable part at the tip thereof, an operating part 10b that includes an angle knob and the like to operate the bendable part of the insertion part 10a, a flexible light guide tube 10c that connects the operating part 10b with a light source apparatus 20, and a connector 10d that is provided at the rear anchor of the flexible light guide tube 10c.

The light source apparatus 20 supplies illuminating light and excitation light to the fluorescence observation endoscope 10, and, as described in detail below, has a function as an image signal generator that generates image signals from signals taken by the fluorescence observation endoscope 10 and a function as a brightness changing means for changing the brightness of at least one image to reduce brightness difference between the normal image and the fluorescence image on the monitor 60 when the fluorescence image and the normal images which have been taken are displayed simultaneously. On the front surface of the light source apparatus 20, there are provided a key switch 22 for ON/OFF operation of a main power supply thereof, and a switch panel 23 on which various kinds of operation switches are arranged.

Hereinafter, according to FIG. 2, the constitutions of the fluorescence observation endoscope 10 and the light source apparatus 20 are explained in sequence. On the distal end surface of the insertion part 10a of the fluorescence observation endoscope 10, there are provided a light distribution lens 11 and an objective lens 12. Inside the tip portion of the insertion part 10a, there are incorporated an imaging device 13 such as a CCD color imaging sensor that takes an object's color image formed by the objective lens 12, an excitation light cut filter 14 that is provided between the imaging device 13 and the objective lens 12 to eliminate the wavelength components equivalent to the excitation light for fluorescence excitation from the wavelength components of light directed to the imaging device 13 from the objective lens 12, and a cable driver 15 that amplifies image signals outputted from the imaging device 13. It is noted that the excitation light cut filter 14 may be arranged closer to an object to be observed than the objective lens 12.

Figure 3:
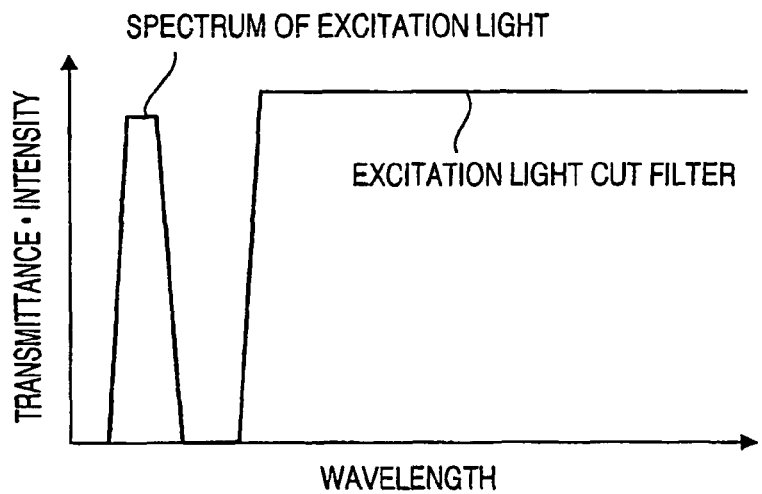
FIG. 3 is a graph illustrating transmission characteristics of an excitation light cut filter provided in an optical system in FIG. 2.

As shown in FIG. 3, the excitation light cut filter 14 has characteristics that cut off the excitation light and transmit light with wavelengths longer than the excitation light. Therefore, it is possible to prevent the excitation light, which is reflected by the wall of the body cavity subject to the observation, from being introduced into the imaging device 13 and to take only the fluorescence images during fluorescence observation. In addition, since near-ultraviolet light that excites autofluorescence of a living organism is applied as excitation light, even if the wavelength components of the excitation light is cut off by the excitation light cut filter 14, there is no trouble in taking a blue component, which is also generally used as excitation light, while taking normal color images.

A signal cable 18 that transmits the image signals amplified by the cable driver 15 runs through the insertion part 10a, the operation part 10b, and the flexible light guide tube 10c, and is connected to a signal processing circuit of the light source apparatus 20 that is connected to the fluorescence observation endoscope 10.

In parallel with the signal cable 18, a light guide 16 that is constituted by bundling plurality of optical fibers runs through the insertion part 10a, the operation part 10b, and the flexible light guide tube 10c. The tip end face of the light guide 16 faces the light distribution lens 11 within the tip portion of the insertion part 10a, and the rear anchor of the light guide 16 is fixed in the state to be inserted into the light source apparatus 20. In addition, a connection part 10d of the fluorescence observation endoscope 10 has a built-in ROM 17 for reading identification data when attached to the light source apparatus 20.

The light source apparatus 20 selectively introduces either white light for observation of the body cavity wall or the excitation light that excites the living tissues of the body cavity wall so that the living tissues emits autofluorescence into the end face of the rear anchor of the light guide 16. The light source apparatus 20 further processes the image signals received from the cable driver 15 to generate video signals, and then outputs the video signals to the monitor 60.

An optical system of the light source apparatus 20 is provided with a white light source (discharge tube lamp) 30 that emits substantially parallel white light (white light), a light control aperture 31 that controls the beam diameter of the white light emitted from the white light source 30, a condenser lens 32 that converges the white light which is transmitted through the light control aperture 31 on the end face of the rear anchor of the light guide 16, an excitation light source 33 that emits the excitation light, an optical waveguide (single mode fiber) 34 that guides the excitation light emitted from the excitation light source 33, a collimating lens 35 that collimates the excitation light, which is diverging light emitted from the optical waveguide 34, and a dichroic mirror 36 that combines both light paths of the white light and the excitation light.

The light control aperture 31 is driven by an aperture driving motor 31a, and functions to control the intensity of the white light according to the reflectance of an object. The white light path that extends straight from the white light source 30 to the light guide 16 and the excitation light path that intersects perpendicularly therewith are combined by the light path combining device, that is, the dichroic mirror 36. Since the dichroic mirror 36 transmits the white light and reflects the near-ultraviolet light with wavelengths shorter than the white light, the dichroic mirror 36 transmits major part of the white light and reflects the excitation light, introducing both kinds of light into a single light path that extends to the end face of the rear anchor of the light guide 16.

Figure 4:
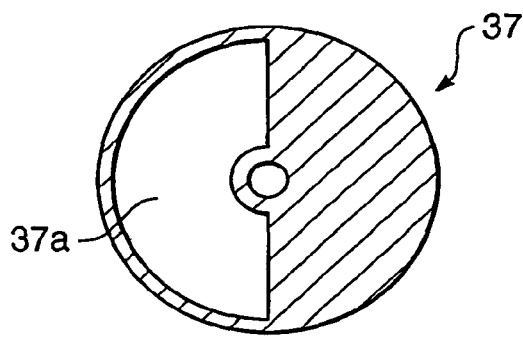
FIG. 4 is a front view of a rotary shutter provided in the optical system in FIG. 2.

Between the white light source 30 and the dichroic mirror 36, there is arranged a rotary shutter 37 that enables the intermittent ON/OFF operation of the white light (that is, intermittently transmits or blocks the white light). The rotary shutter 37, as a front view thereof is shown in FIG. 4, has a fan-shaped window 37a with a center angle of 180 degrees, and the size of the window 37a is configured to be larger than the diameter of the beam of the white light. The rotary shutter 37 is allowed to rotate and intermittently transmit the white light as a shutter driving motor 38 is driven.

The light source apparatus 20 is provided with a lamp driving power supply 51 that supplies current to the white light source 30, a laser driver 52 that drives and switches the excitation light source 33, a first motor driver 53 that drives the aperture driving motor 31a, a second motor driver 54 that drives the shutter driving motor 38, and a CCD driver 56 that drives the imaging device 13. The light source apparatus 20 further includes a pre-signal-processing circuit 57 that processes image signals received from the cable driver 15, first and second memories 58a and 58b that temporarily store digital image signals outputted from the pre-signal-processing circuit 57, a post-signal-processing circuit 59 that transforms the digital image signals outputted from the image memories into standardized video signals which are allowed to be displayed on a television monitor and outputs the standardized video signals, and a system controller 70 and a timing controller 71 that control all of the above components.

The system controller 70 is connected with a fluorescence mode switch 73 provided at the operation part 10b, and is further connected electrically with various switches that are arranged on the switch panel 23. Based on the setting of each switches, the system controller 70 controls the lamp driving power supply 51 and the laser driver 52 so that the white light and the excitation light are emitted consecutively or stopped, and further switches a display on the monitor 60.

Figure 5:
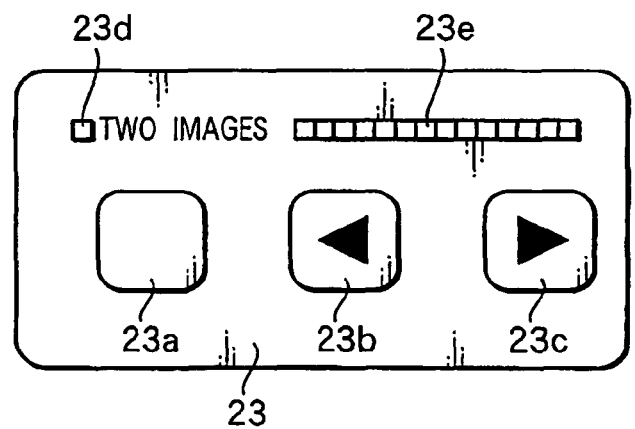
FIG. 5 is a schematic diagram illustrating constitution of a switch panel of the system shown in FIG. 2.

On the switch panel 23, as shown in FIG. 5, there are provided a fluorescence mode display button 23a for selecting images to be displayed in the fluorescence mode—only the fluorescence image or both the fluorescence image and the normal image that are simultaneously displayed side by side, and a pair of brightness setting buttons 23b and 23c for down/up, respectively. In addition, the switch panel 23 is provided with a two-image-indicator 23d which lights up when both the fluorescence image and the normal image that are simultaneously displayed side by side are selected in the fluorescence mode and a setting level indicator 23e which visually indicates a target value for the brightness of the fluorescence image and the normal image set by operating the brightness setting buttons 23b and 23c.

When the fluorescence observation endoscope 10 is connected to the light source apparatus 20, the built-in ROM 17 inside the fluorescence observation endoscope 10 is also connected to the system controller 70, which identifies that what is connected to the light source apparatus 20 is the fluorescence observation endoscope 10 by reading the identification data stored in the ROM 17.

Based on a command from the system controller 70, the timing controller 71 controls the laser driver 52 to carry out the intermittent ON/OFF operation of the excitation light at predetermined timing, and further controls the second motor driver 54 that drives the shutter driving motor 38 to carry out the intermittent ON/OFF operation of the white light at predetermined timing. The timing controller 71 also controls the timing when the imaging device 13 takes an image through the CCD driver 56, and further controls the data read/write operation of each of the image memories 58a and 58b (the address data controls), indicating the respective timings of the image signal processing for the pre-signal-processing circuit 57 and the post-signal-processing circuit 59.

Next, the internal constitution of the system controller 70 and the pre-signal-processing circuit 57 that are configured to change the brightness of the images will be described with reference to a block diagram shown in FIG. 6. The system controller 70 is provided with a setting table 70a that defines a target value for the brightness of the normal image and the fluorescence image set by operating the brightness setting buttons 23b and 23c on the switch panel 23 and first and second comparators 70b and 70c that compare the brightness of each of the normal image and the fluorescence image with the target value.

Furthermore, the pre-signal-processing circuit 57 is provided with a A/D converter 57a that converts analog fluorescence image signals YUV outputted from the imaging device 13 while taking the fluorescence image and analog normal image signals R, G, B outputted from the imaging device 13 while taking the normal image to corresponding digital signals, a first brightness converting circuit 57b that converts digitally-converted color signals of the normal image to brightness signals, a first detector 57c that detects the brightness of the images by analyzing the histogram of the brightness signals, a second brightness converting circuit 57*d* that converts digitally-converted signals of the fluorescence image to brightness signals, a second detector 57*e* that detects the brightness of the fluorescence image by analyzing the histogram of the brightness signals, and a multiplier 57*f* that amplifies or attenuates digitally-converted image signals.

Next, the operation of the endoscope system of the first embodiment constituted as mentioned above is explained. The endoscope system of the embodiment operates in any one of the following three modes as moving image modes: a normal image display mode in which the normal (color) image taken with the white light applied continuously is displayed as a moving image; a fluorescence image display mode in which the fluorescence image taken with the excitation light applied continuously is displayed as a moving image; and a simultaneous display mode in which the normal image and the fluorescence image taken with the white light and the excitation light alternately applied are displayed as moving images. When a fluorescence mode switch 73 provided at the operation part 10*b* of the fluorescence observation endoscope 10 is OFF, the system is set up in the normal image display mode. If the fluorescence mode switch is turned ON, the system will be set up in either the fluorescence image display mode or the simultaneous display mode. It can be previously defined by operating the fluorescence mode display button 23*a* that are provided on the switch panel 23 which mode will be selected. Hereinafter, each mode is explained.

When the fluorescence mode switch 73 is OFF, the system is set up in the normal image display mode, as described above. In the normal image display mode for the normal observation, the system controller 70 controls the lamp driving power supply 51 to let the white light source 30 emit the white light continuously. At this time, the shutter driving motor 38 and the excitation light source 33 are not driven, but still OFF. The rotary shutter 37 stops with the window 37*a* located on the path of the white light such that the white light is transmitted through the shutter 37. Thereby, the white light emitted from the white light source 30 is continuously introduced into the light guide 16. The imaging device 13 provided at the tip of the fluorescence observation endoscope captures the image of the inside of the body cavity illuminated with the white light. The normal image signals outputted from the imaging device 13 are inputted into the pre-signal-processing circuit 57 through the cable driver 15 and the signal cable 18.

The pre-signal-processing circuit 57, based on the signals from the timing controller 71, allows the first image memory 58*a* and the second image memory 58*b* to store the normal image signals. The post-signal processing circuit 59, based on the signals from the timing controller 71, reads out the image signals from the first image memory 58*a* and the second image memory 58*b*, and converts the image signals into the video signals, displaying a single moving normal image in full screen on the monitor 60. FIG. 7 shows an example of a screen displayed on the monitor 60 in a normal image display mode.

In the normal image display mode, the first comparator 70*b* of the system controller 70 compares the target value defined in the setting table 70*a* with the brightness of the normal image outputted from the first detector 57*c* of the pre-signal-processing circuit 57 to adjust the intensity of the white light by controlling the first motor driver 53 that drives the aperture driving motor 31*a* on the basis of the comparison result. As shown in FIG. 6, moreover, the first comparator 57*b* is connected with an aperture opening detector 31*b* that detects the opening level of the light control aperture 31, and receives a detection result from the aperture opening detector to drive the first motor driver 53 under closed-loop control.

If the fluorescence mode switch 73 is turned ON in the normal image display mode, the system will be set up in either mode between the fluorescence image display mode and the simultaneous display mode, the mode which is previously defined by the fluorescence mode display button 23*a* on the switch panel 23. When the system is set up in the fluorescence image display mode by the fluorescence mode display button 23*a* on the switch panel 23, the system controller 70 controls the lamp driving power supply 51 to turn OFF the white light source 30, and further controls the laser driver 52 to let the excitation light source 33 emit the excitation light continuously. The shutter driving motor 38 is still OFF. Thereby, the excitation light emitted from the excitation light source 33 is continuously introduced into the light guide 16. The imaging device 13 provided at the tip of fluorescence observation endoscope captures the image of fluorescence emitted from the body cavity excited by the excitation light. The fluorescence image signals outputted from the imaging device 13 are inputted into the pre-signal-processing circuit 57 through the cable driver 15 and the signal cable 18.

The pre-signal-processing circuit 57 allows the first and second memories 58*a*, 58*b* to store the fluorescence signals, based on the signals from the timing controller 71. The post-signal-processing circuit 59, based on the signals from the timing controller 71, reads out the image signals from the first and second memories 58*a*, 58*b* to convert the image signals into the video signals, displaying a single fluorescence image as a moving image on the monitor 60 in a full screen view coinciding with the display area of the monitor 60.

The second comparator 70*c* of the system controller 70 compares the target value defined in the setting table 70*a* with the brightness of the fluorescence image outputted from the second detector 57*e* of the pre-signal-processing circuit 57, and based on the comparison result, controls the laser driver 52 for driving the excitation light source 33 to adjust the emission amount of the excitation light source 33 in the first stage, and further controls the multiplier 57*f* to change the gain of the fluorescence image signals in the case where the only controlling of the emission amount is not enough to attain the target value in the second stage. Since the fluorescence image generally tends to be obscure, the fluorescence emission amount is increased by increasing the emission amount of the excitation light source 33 in the first stage, and if necessary, the fluorescence image signals are amplified. Since it is needed to judge the brightness of the fluorescence image in consideration of the gain changed by the multiplier 70*f*, the multiplier 70*f* is arranged in the preceding step of the second brightness conversion circuit 57*d*.

When the fluorescence mode switch 73 is turned ON and the simultaneous display mode is applied by the fluorescence mode display button 23*a*, the system controller 70 controls the lamp driving power supply 51 to let the white light source emit continuously. The timing controller 71 controls the second motor driver 54 to rotate the shutter driving motor 38, and further controls the laser driver 52 to turn OFF the excitation light source 33 while the window 37*a* of the rotary shutter 37 is located on the white light path (while the white light is introduced into the light guide) and generate the excitation light while the shielding part of the rotary shutter 37 is located on the white light path (while the white light is not introduced into the light guide). Thereby, an object is irradiated alternately with the white light and the excitation light. The imaging device 13 provided at the tip of the fluorescence observation endoscope alternately takes the normal image of the body cavity wall illuminated with the white light and the fluorescence image of the body cavity wall excited by the excitation light. The image signals outputted from the imaging device 13 is inputted into the pre-signal-processing circuit 57 through the cable driver 15 and the signal cable 18.

FIG. 8 is a chart pattern showing the respective irradiation timings of the white light and the excitation light in the simultaneous display mode and the timing when image data is outputted from the imaging device 13. As shown in FIG. 8, the normal color image is taken while the white light is applied and the excitation light is not applied, and the fluorescence image is taken while the white light is not applied and the excitation light is applied.

Based on the signals from the timing controller 71, the pre-signal-processing circuit 57 allows the first image memory 58a to store the normal image signals and the second memories to store the fluorescence image signals. Based on the signals from the timing controller 71, the post-signal-processing circuit 59 reads out the respective image signals from the first and second memories, and performs scan conversion for the respective image signals, which are then displayed as a moving normal image and a moving fluorescence image on the monitor 60, respectively. FIG. 9 shows an example of a screen displayed on the monitor 60 in the simultaneous display mode.

In the simultaneous display mode, the first comparator 70b of the system controller 70 does not receive the target value from the setting table 70a, and instead compares the brightness of the normal image outputted from the first detector 57c with the brightness of the fluorescence image outputted from the second detector 57e, and based on the comparison result, the first motor driver 53 is controlled to adjust the intensity of the white light such that the brightness of the normal images is substantially equal to the brightness of the fluorescence image.

According to the above-mentioned first embodiment, when the normal image and the fluorescence image are displayed side by side on the single monitor 60, by narrowing down the light control aperture 31 in conformity with the brightness of the fluorescence image to reduce the intensity of the white light, it is possible to set the brightness of the normal image substantially equal to the brightness of the fluorescence image and prevent observer's fatigue caused by the brightness difference. However, it is noted that since too obscure normal image poses a problem for observation, the brightness of the normal image needs not to be completely the same as the brightness of the fluorescence image unless the brightness difference between both kinds of images causes observer's fatigue.

Figure 10:
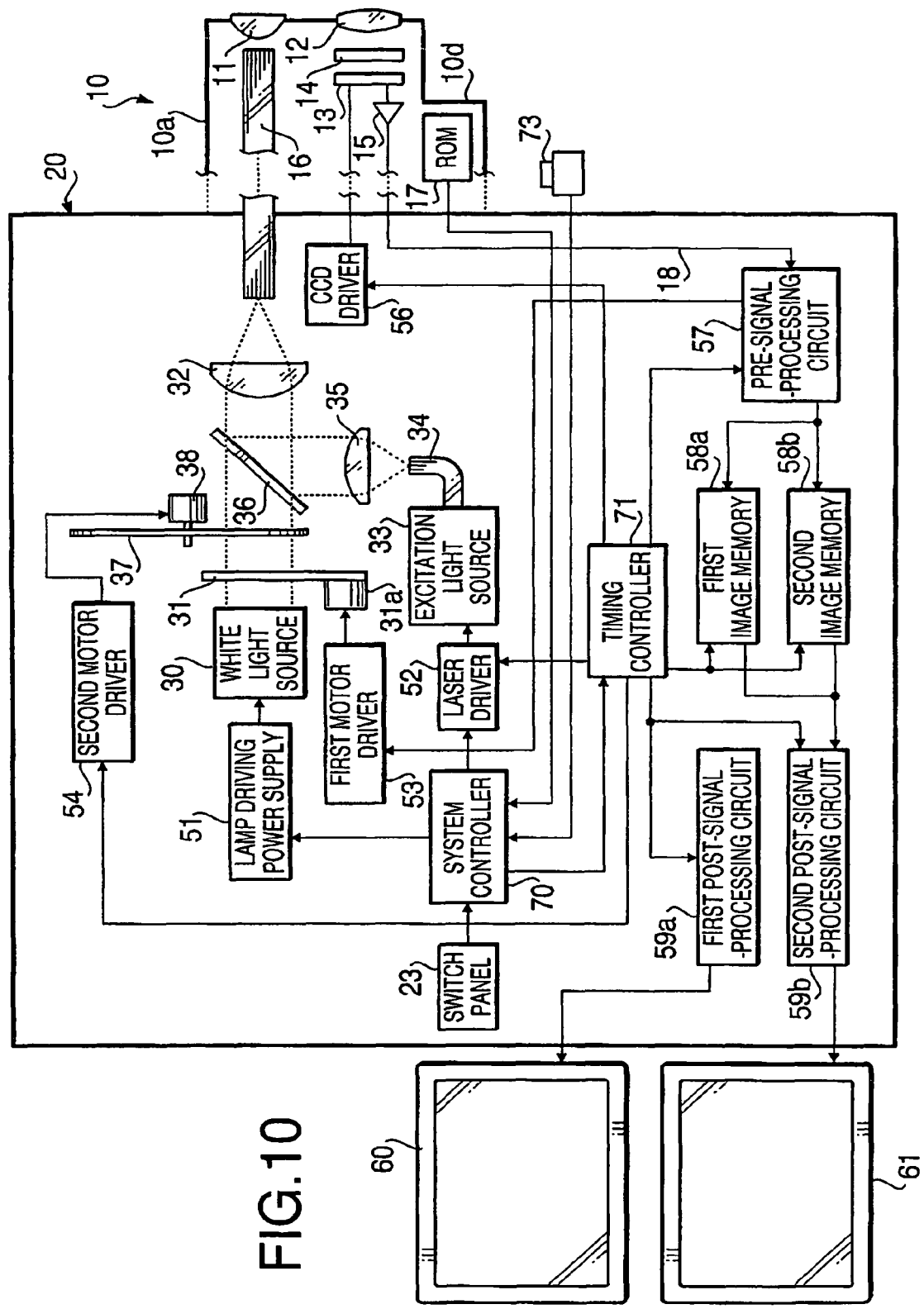
FIG. 10 is a block diagram illustrating internal constitution of an electronic endoscope system according to a second embodiment of the invention.
Figure 11:
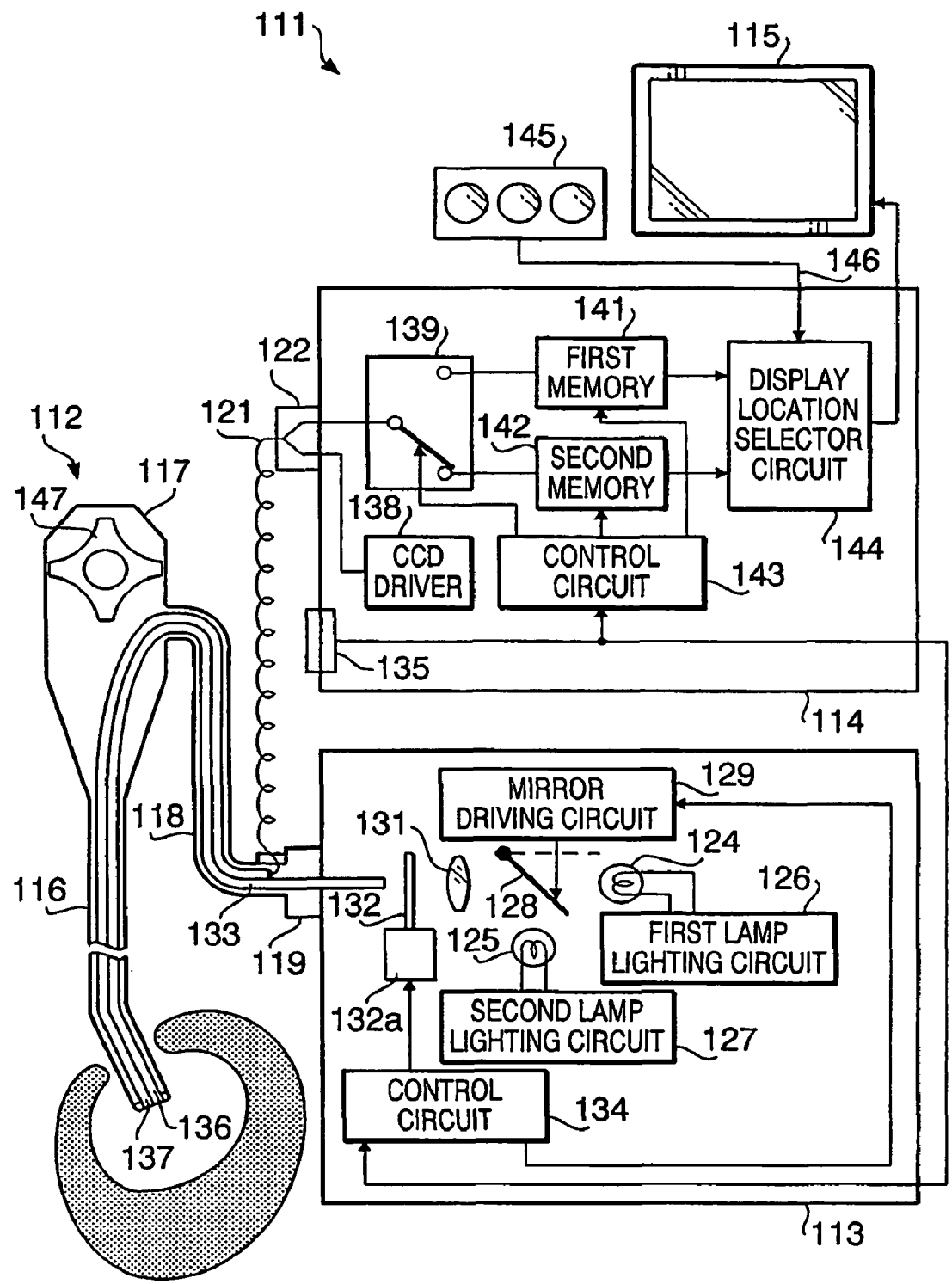
FIG. 11 is a block diagram showing a configuration of a conventional electronic endoscope system.

FIG. 10 is a block diagram illustrating internal constitution of an electronic endoscope system according to a second embodiment of the invention. The constitution of the system has the difference with the first embodiment shown in FIG. 2 in being provided with two monitors 60 and 61 and corresponding post-signal-processing circuits 59a and 59b for the monitors 60 and 61. The constitution other than the above features is the same as the first embodiment.

In the system of the first embodiment, when the normal image and the fluorescence image are displayed simultaneously in the simultaneous display mode, both kinds of images are displayed side by side on the single monitor 60. Therefore, a displaying area for each image is small, and it is more difficult to confirm details than a case of full-screen display of a single image. To solve this problem, in the system of the second embodiment, the normal image and the fluorescence image are displayed in full-screen on the first and second monitors 60 and 61, respectively, in the simultaneous display mode.

Figure 6:
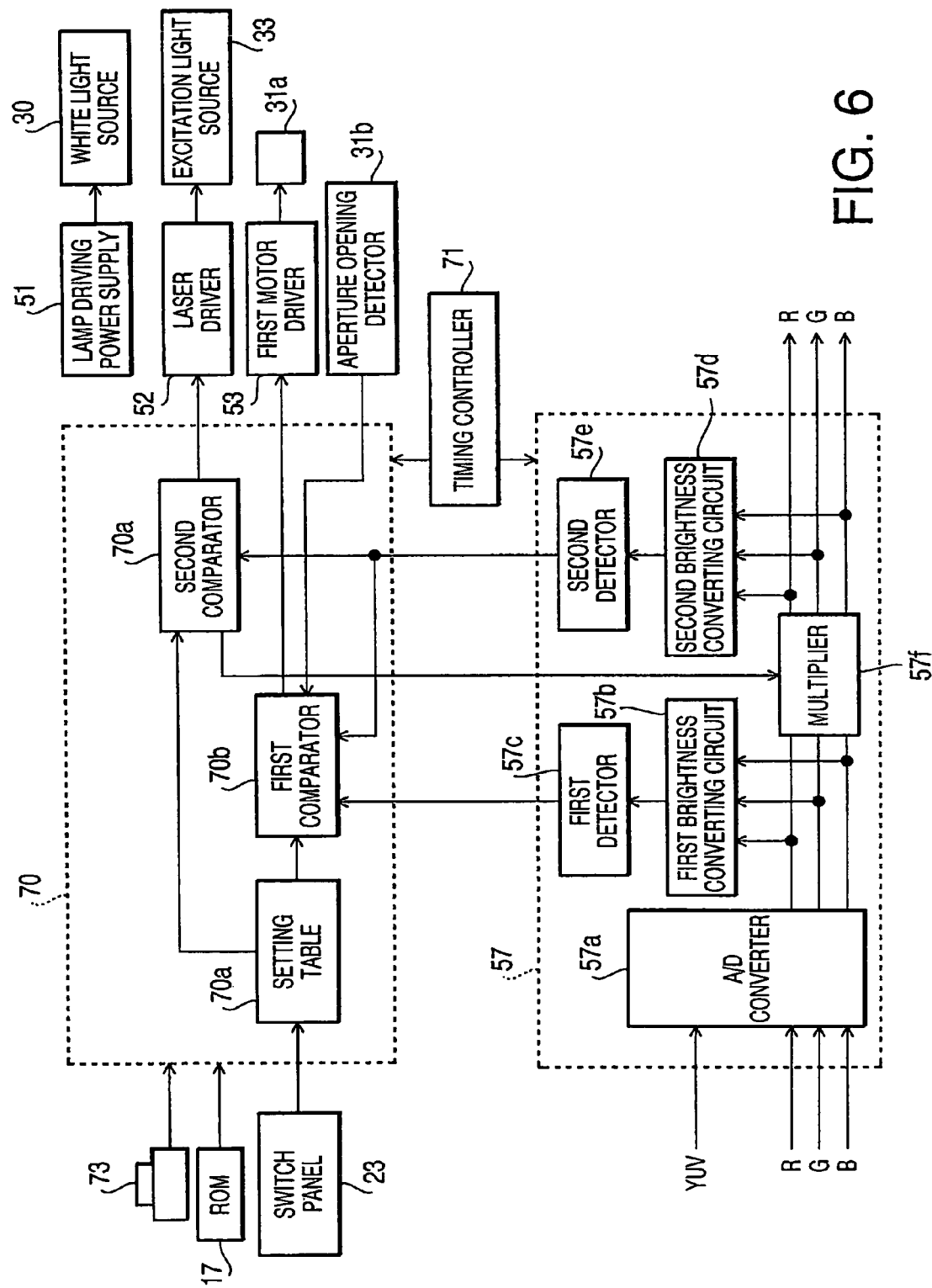
FIG. 6 is a block diagram illustrating internal constitution of a system controller and a pre-signal-processing circuit of the system shown in FIG. 2

In addition, a system controller 70 and a pre-signal-processing circuit 57 are configured to be the same as the constitution of the first embodiment shown in FIG. 6, and controls the brightness of the normal image displayed on the monitor 60 to be substantially equal to the brightness of the fluorescence image displayed on the monitor 61. Thereby, it is possible to reduce observer's fatigue owing to no brightness difference while watching both monitors.

When two monitors are used as described in the second embodiment 60, an identical effect can be obtained by adjusting the brightness of each monitor. However, it is noted that in the normal image display mode or the fluorescence image display mode, assumed is a case where for example, a doctor providing medical treatment and a nurse supporting the doctor observe the same image on different monitors, respectively. Accordingly, it is not possible to completely define which image is displayed on which monitor, and it is troublesome to manually adjust the brightness of the monitor every time a mode is changed. Since the constitution of the second embodiment enables to previously set the brightness of one of the two monitors the same as the brightness of the other and automatically adjust the brightness of each image at the side of the light source apparatus 20, it is possible to observe the images with appropriate brightness without troublesome operation.

The present disclosure relates to the subject matter contained in Japanese Patent Application No. P2004-215597, filed on Jul. 23, 2004, which is expressly incorporated herein by reference in its entirely.

What is claimed is:

1. An electronic endoscope system used for observing living tissues inside a body cavity, comprising:
    an image capturing system capable of capturing at least a normal image and a fluorescence image of the living tissues;
    an illuminating device having a white light source emitting white light and an excitation light source that emits excitation light having a predetermined wavelength, the living tissues emitting autofluorescence when irradiated with the excitation light;
    at least one display device configured to display the normal image and the fluorescence image; and
    a brightness control system configured to adjust brightness of at least one of the normal image and the fluorescence image to reduce a brightness difference between the normal image and the fluorescence image to be displayed
    wherein the brightness control system includes:
        brightness detectors configured to detect the brightness of the normal image and the fluorescence image;
        a setting system configured to define a target value for the brightness of the normal image and the fluorescence image respectively; and
        a brightness comparing system configured to compare the brightness of at least one of the normal image and the fluorescence image with the target value defined by the setting system,
        the brightness control system controlling the brightness of at least one of the normal image and the fluorescence image that is displayed on the display device, which is detected by one of the brightness detectors, to be substantially equal to the target value defined by the setting system.

2. The electronic endoscope system according to claim 1, wherein the
    brightness comparing system is configured to compare the brightness between the normal image and the fluorescence image when the normal image and the fluorescence image are displayed simultaneously.

3. The electronic endoscope system according to claim 2, wherein the normal image and the fluorescence image are displayed simultaneously on the same display device.

4. The electronic endoscope system according to claim 2, wherein the normal image and the fluorescence image are displayed simultaneously on the separate display devices, respectively.

5. The electronic endoscope system according to claim 1, wherein the brightness control system includes a white light control system configured to control the intensity of the white light to adjust the brightness of the normal image.

6. The electronic endoscope system according to claim 5, wherein the white light control system includes an aperture control system configured to drive a light control aperture that changes the beam diameter of the white light to control the intensity of the white light.

7. The electronic endoscope system according to claim 6, wherein the aperture control system includes an aperture opening detector configured to detect the opening level of the light control aperture, the aperture control system using a detection result from the aperture opening detector to drive the light control aperture under closed-loop control.

8. The electronic endoscope system according to claim 1, wherein the brightness control system includes an excitation light control system configured to control the emission amount of the excitation light to adjust the brightness of the fluorescence image.

9. The electronic endoscope system according to claim 1, wherein the brightness control system includes a multiplier configured to amplify or attenuate fluorescence image signals to adjust the brightness of the fluorescence image.

10. The electronic endoscope system according to claim 1, further including a ROM that stores an identification data for identifying what kind of electronic endoscope connected to the illuminating device.

11. The electronic endoscope system according to claim 1, wherein the illuminating device includes a rotary shutter provided in front of the white light source, the rotary shutter having a light transmitting area and a light blocking area, the white light intermittently illuminating the living tissues as the rotary shutter rotates.

12. The electronic endoscope system according to claim 11, wherein the illuminating device includes an excitation light source driver that intermittently turns ON/OFF the excitation light source synchronously with blocking/transmitting of the white light.

13. The electronic endoscope system according to claim 1, wherein the image capturing system includes:
 an objective lens that receives light from the living tissues and forms an image thereof;
 an imaging device that receives the formed image and outputs an image signal corresponding to the received image; and
 an excitation light cut filter configured to eliminate the wavelength components equivalent to the excitation light from light directed to the imaging device.

14. The electronic endoscope system according to claim 13, wherein the excitation light cut filter is provided between the imaging device and the objective lens.

15. The electronic endoscope system according to claim 13, wherein the excitation light source emits near-ultraviolet light.

* * * * *